United States Patent
Landon et al.

(10) Patent No.: US 11,386,990 B1
(45) Date of Patent: Jul. 12, 2022

(54) THREE-DIMENSIONAL SELECTIVE BONE MATCHING

(71) Applicant: Smith & Nephew, Inc., Memphis, TN (US)

(72) Inventors: Ryan L. Landon, Olive Branch, MS (US); Daniel Farley, Memphis, TN (US); David Lieberman, Cordova, TN (US)

(73) Assignee: Smith & Nephew, Inc., Memphis, TN (US)

(*) Notice: Subject to any disclaimer, the term of this patent is extended or adjusted under 35 U.S.C. 154(b) by 342 days.

(21) Appl. No.: 16/387,151

(22) Filed: Apr. 17, 2019

Related U.S. Application Data

(60) Provisional application No. 62/658,988, filed on Apr. 17, 2018.

(51) Int. Cl.
*G16H 30/40* (2018.01)
*A61B 8/08* (2006.01)
(Continued)

(52) U.S. Cl.
CPC ......... *G16H 30/40* (2018.01); *A61B 8/5246* (2013.01); *A61B 34/10* (2016.02); *G06T 19/20* (2013.01); *A61B 2034/105* (2016.02); *A61B 2034/108* (2016.02); *G06T 15/00* (2013.01); *G06T 2200/04* (2013.01); *G06T 2200/08* (2013.01);
(Continued)

(58) Field of Classification Search
CPC .............. G16H 30/40; G06T 19/20; G06T 2207/10116; G06T 2200/04; G06T 2207/10081; G06T 2200/08; G06T 15/00; A61B 34/10; A61B 8/5246; A61B 2034/105; A61B 2034/108
See application file for complete search history.

(56) References Cited

U.S. PATENT DOCUMENTS

| | | | | |
|---|---|---|---|---|
| 2004/0120469 | A1* | 6/2004 | Hebecker | G06T 11/003 378/210 |
| 2010/0256479 | A1* | 10/2010 | Park | B33Y 80/00 600/410 |

(Continued)

FOREIGN PATENT DOCUMENTS

| | | |
|---|---|---|
| WO | 2016116946 A2 | 7/2016 |
| WO | 2019180745 A1 | 9/2019 |
| WO | 2019180746 A1 | 9/2019 |

OTHER PUBLICATIONS

YouTube video, "X-rays part 1—Dr. Paul Siffri" by SHCCvideo Hoyle, Apr. 2, 2012. https://www.youtube.com/watch?v=0t5gxD99q4E (Year: 2012).*

*Primary Examiner* — Sing-Wai Wu
(74) *Attorney, Agent, or Firm* — KDB Firm PLLC

(57) ABSTRACT

Method, system, and program products are disclosed herein for creating a 3D model based on a plurality of received 2D medical images. Once the 2D images are received, a determination is made regarding any potential processing steps required to put the images into a standard view. Once the images are processed, a plurality of points are identified that are associated with a portion of an anatomical landmark. Various historical 2D images are then identified based on a comparison between the plurality of points. Using the historical information, a 3D image is generated of an anatomical feature of a patient.

20 Claims, 17 Drawing Sheets

(51) Int. Cl.
*A61B 34/10* (2016.01)
*G06T 19/20* (2011.01)
*G06T 15/00* (2011.01)

(52) U.S. Cl.
CPC ............... *G06T 2207/10081* (2013.01); *G06T 2207/10116* (2013.01)

(56) References Cited

U.S. PATENT DOCUMENTS

| | | | |
|---|---|---|---|
| 2014/0228860 A1* | 8/2014 | Steines | A61B 34/10 |
| | | | 606/130 |
| 2016/0239632 A1* | 8/2016 | Yu | G16H 50/50 |
| 2017/0018082 A1* | 1/2017 | Hu | G06T 15/08 |
| 2017/0258526 A1 | 9/2017 | Lang | |
| 2017/0323443 A1* | 11/2017 | Dhruwdas | G06T 7/0012 |

\* cited by examiner

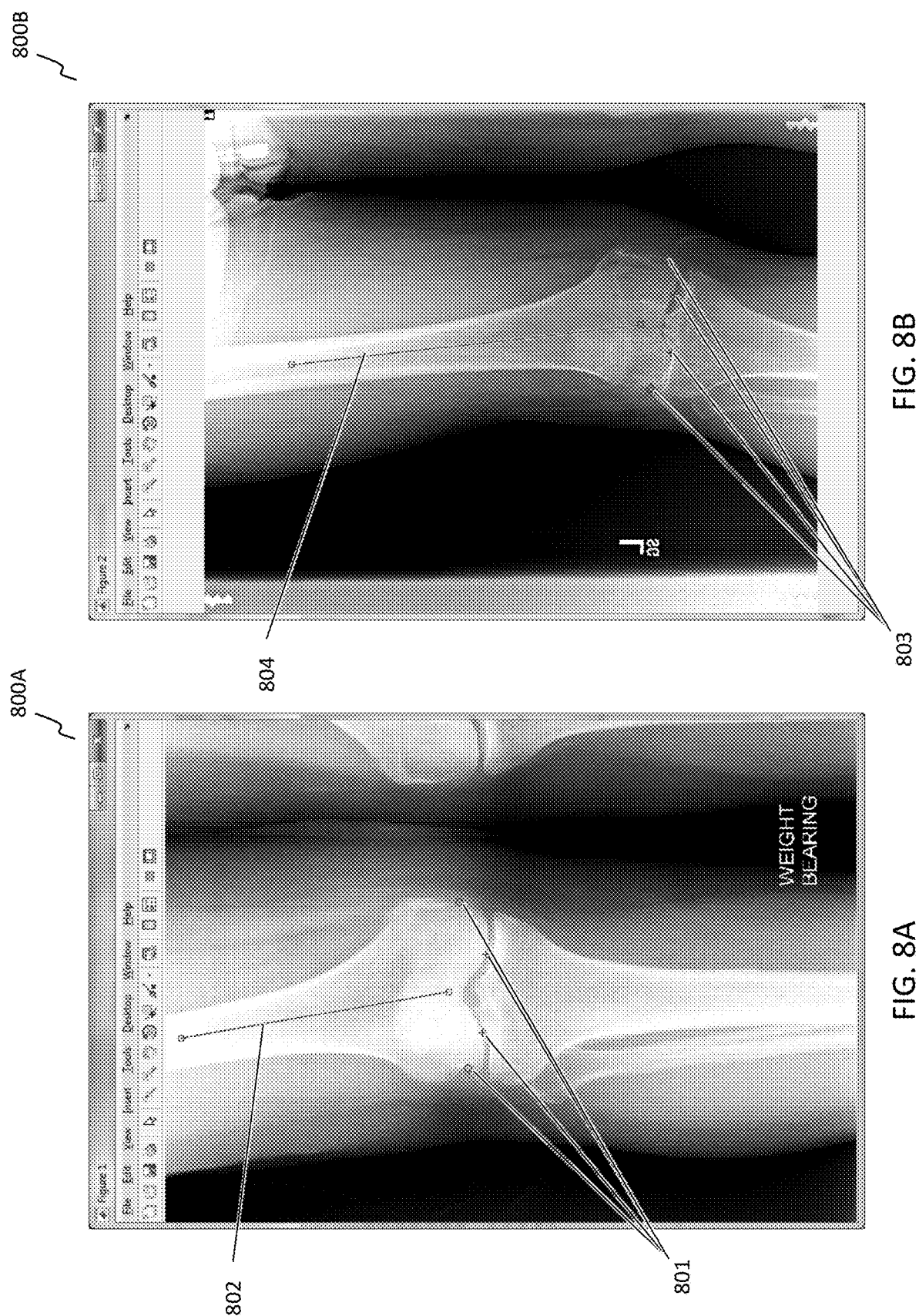

THREE-DIMENSIONAL SELECTIVE BONE MATCHING

CROSS-REFERENCE TO RELATED APPLICATIONS

This application claims the priority benefit of U.S. Provisional Patent Application No. 62/658,988, filed Apr. 17, 2018 and entitled "THREE-DIMENSIONAL GUIDE WITH SELECTIVE BONE MATCHING," the contents of which are incorporated herein by reference in its entirety.

TECHNICAL FIELD

The invention relates to methods of creating 3D anatomical models from bi-planar 2D images.

BACKGROUND

As the cost of providing healthcare has continued to rise, many entities are looking for ways to reduce costs. In some cases, insurance companies impose more stringent reimbursement criteria in order to shift away from more expensive treatments. For example, insurance providers may question whether the use of magnetic resonance imaging (MRI) equipment is necessary because of the high cost of using such equipment as compared to other imaging systems, including computed tomography (CT) scanners and X-ray machines. In other cases, less populated or emerging markets may not have access to MRI technology because of the cost of obtaining and operating such systems.

Currently, many patient-specific total joint replacement systems, including Smith & Nephew's VISIONAIRE cutting guides, depend upon the ability to interpret a patient's joint anatomy from a sequence of images produced by an MRI scan. In particular, patient-specific joint replacement procedures require form-fitting surfaces matched to areas that include cartilage surfaces, such as in the knee. MRI scans, which provide three dimensional images of a scanned anatomical feature including soft tissue, are currently required because other imaging technologies provide insufficient detail for the development of such surfaces. VISIONAIRE is a registered trademark of Smith & Nephew, Inc. of Memphis, Tenn.

Furthermore, the process of converting MRI data into a patient-specific joint replacement instrument may require a significant amount of user intervention and data processing prior to manufacturing the instrument. A user often spends a significant amount of time ensuring that a bone model created using the MRI data matches the patient's bone as closely as possible. In short, the reliance on MRI scans can either preclude certain patients from receiving a joint replacement if an MRI system is not available or inhibit or delay the approval process if an insurance provider denies coverage and requests that other treatments be pursued in advance of total joint replacement.

The invention described herein is a technology aimed to support in the creation of a bone guide based on x-ray images, which may be referred to as a variable bone coupler. It is intended that this technology may facilitate a guide system for joint replacement that is not sensitive to changes in MRI reimbursement and would be available to markets where MRI scans are not readily available.

BRIEF DESCRIPTION OF THE DRAWINGS

For the purpose of illustrating the invention, there is shown in the drawings various embodiments. It being understood, however, that the invention is not limited to the specific instrumentalities disclosed as they are used for illustrative purposes only. Included in the drawings are the following Figures:

FIG. 8A depicts another illustrative example of one or more 2D medical images in accordance with an embodiment.

FIG. 8B depicts another illustrative example of one or more 2D medical images in accordance with an embodiment.

DETAILED DESCRIPTION

Figure 1:
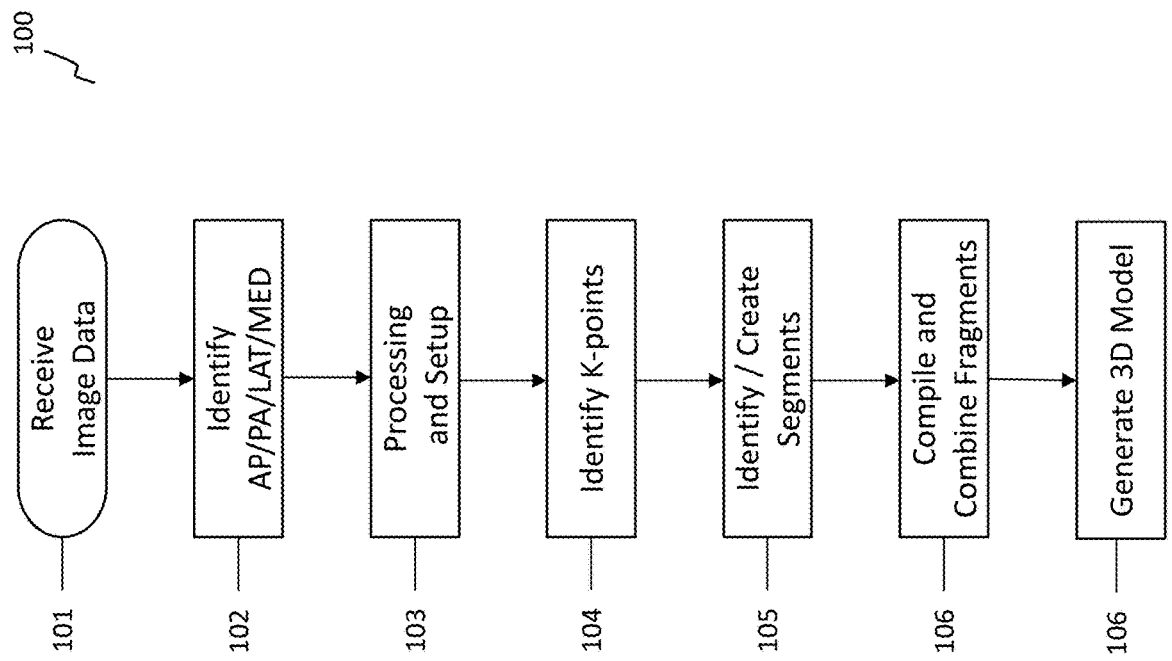
FIG. 1 depicts an illustrative method for generating a 3D model based on 2D patient image data in accordance with an embodiment.
Figure 2B:
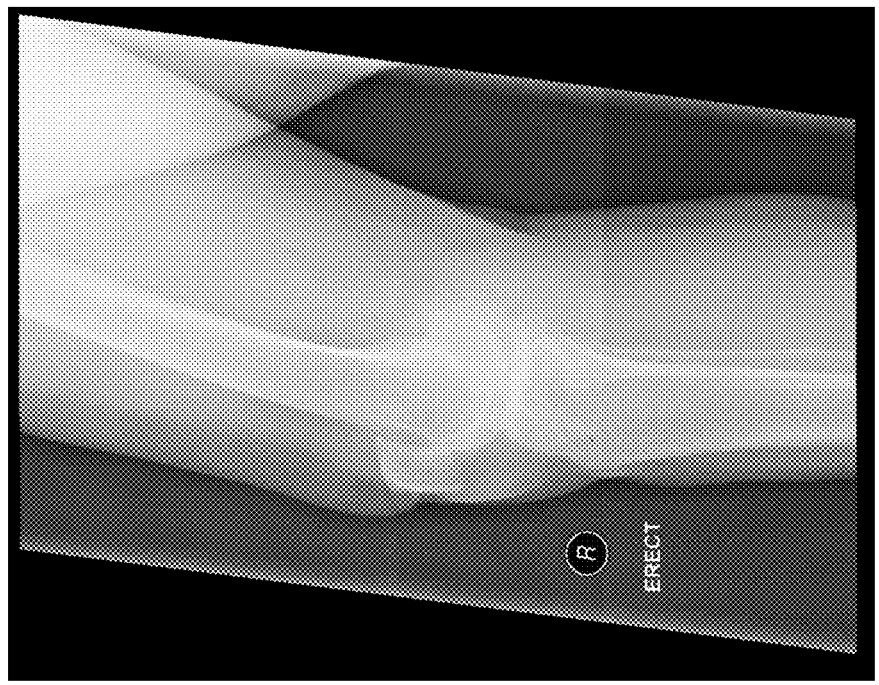
FIG. 2B depicts another illustrative example of one or more 2D medical images in accordance with an embodiment.
Figure 2A:
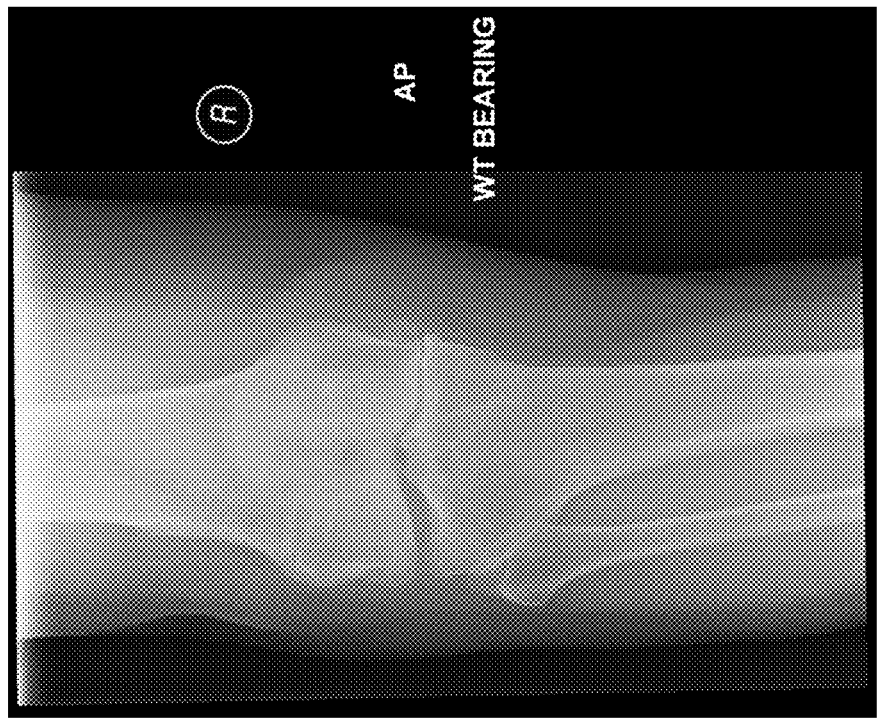
FIG. 2A depicts an illustrative example of one or more 2D medical images in accordance with an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Moreover, the present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As discussed herein, an embodiment may allow for the creation of 3D models from 2D image data that can be more easily acquired than volumetric image data such as MRI or CT. 3D models may include one of CAD, IGES, STL, VRML, DXF, OBJ, or similar files. In some embodiments, subdivision of an anatomical model may create a large library of bone shapes, i.e., more than are available with standard statistical shape model (SSM) techniques. Thus, the semi-automated system as discussed herein may require input from an imaging expert who provides quality control.

Referring now to FIG. 1, an example embodiment 100 may receive a plurality of 2D images of an anatomical feature of a patient 101. In a further embodiment, the anatomical feature (i.e., landmark) may be at least one of an epicondyle, a tibial spine, Whiteside's line, a trans-epicondylar axis, tibial tuberosity, a mechanical axis, an anatomic axis, the medial malleolus, the adductor tubercle, or any other useful anatomical feature known now or in the future. In another embodiment, the received image data may comprise any form of 2D patient image data, such as, for example, X-ray data, fluoroscopy image data, projectional radiograph data, 2D computed tomography images, 2D echocardiography images, and the like. As further discussed herein, the image data may be acquired by a healthcare provider (e.g., surgeon, clinician, nurse, etc.), by a service provider (e.g., healthcare manufacturer), and/or by a third party healthcare source (e.g., a previous hospital, ambulatory surgery center, etc.).

Once the patient image data is received 101, the various images are reviewed and analyzed to ensure proper view, orientation, shape, and classification, and to determine whether the one or more 2D images require further processing 102. Thus, in an embodiment, a processor may evaluate the provided images to identify whether the provided images are one or more of: a coronal view, a sagittal view, a posterior/anterior (PA) view, an anterior/posterior (AP) view, a lateral to medial (LAT) view, a medial-to-lateral (MED) view, a load bearing view, and/or a non-load bearing view.

In one embodiment, the review and analysis of the various 2D images 102 may be done autonomously by using one or more known image analysis techniques including, but not limited to, object recognition, image segmentation, single particle tracking, and the like. In a further embodiment, the system may request or prompt a user to input additional information. It should be understood by those of ordinary skill in the art, that the additional user input may be used to correct or improve the existing software-based analysis. Moreover, in an alternative embodiment, the analysis 102 may be entirely or primarily based on the user input. For example, the plurality of 2D images may contain an advanced deformity or may not be within the bounds of the analysis software.

Once the images are reviewed 102 and a determination has been made as to whether further processing is required, one or more of the 2D patient images may be processed or enhanced 103. As discussed further herein (e.g., with reference to FIGS. 2-9), one or more features of the 2D patient image data may be moved, cropped, rotated, flipped, lightened, darkened, highlighted, and/or identified. In a further embodiment, a plurality of points at or near the expected resections, mid planes, intersection points, and size and direction extremes (e.g., K15 points, bony landmarks, anatomic landmarks, etc.) may be identified 104 within the processed (i.e., updated) plurality of images. In a further embodiment, the plurality of identified points are related to features and/or associated with a portion of an anatomical feature or landmark. Various examples of anatomical landmarks are discussed herein.

In some embodiments, each of the plurality of points may be associated with a subdivided segment. These points, or control points, may be linked to certain anatomic features, such as, for example, the knee center, posterior points on the lateral and medial condyles, an anterior notch point, the lateral and medial epicondyles, points along the femoral AP axis, or the like. Additionally or alternatively, the control points may be linked to, for example, the custom points on the tibia, knee center, lateral and medial low points on the plateau, tibial tubercle, etc.

In one embodiment, the number and location of control points may correspond to the number and location of vertices on the surface of a tessellated bone model. In an additional embodiment, the number of control points may be predetermined, and the tessellated bone model may be disassembled to create the corresponding number of vertices. In some embodiments, the control points may be used for localized morphing of the associated bone shapes. As such, manipulation of the handles may alter the shape of the associated sub-segment. For example, the handles could be moved in a direction of greatest variation across bone shapes in the historical library, thereby allowing the final bone shape to comprise a combination of scaled and interpolated bone segments from the input library based on the region of bone associated with the handle.

Based on the identified points, the anatomical feature(s) of the patient (i.e., the feature(s) depicted in the received image data 101) are segmented into a number of portions 105. Thus, in some embodiments, an anatomical area, which is adjacent to one of the plurality of points, may be mapped or modeled based on the received plurality of images 101. In a further embodiment, a virtual model (e.g., a plurality of estimated values and markers relative to the adaptively derived point(s)) may be created for each segmented portion 105, such that each segment may have one or more characteristics or a shape as dictated by the analysis of the 2D images compared to the virtual model (e.g., steps 102, 103, and 104 of FIG. 1).

In an embodiment, the components of the virtual model may be compared with a library of historical 2D medical images. It should be understood, that any of the various methods of image analysis discussed herein may be utilized to determine and/or identify which, if any, of the images in the historical library closely match the received image data 101. Accordingly, all, or a portion, of the received 2D patient images 101 may be compared with existing 2D patient images to find a best fit or best match. Once a best-fitting historical image(s) is identified, one or more 3D patient images may be accessed that directly correlate to the historical 2D image. Thus, in some embodiments, the library of historical medical images contains one or more 3D images that correspond to each 2D patient image. Stated differently, if a patient were to visit a hospital or medical facility and have both 2D and 3D images taken of their anatomy, those images may be stored in the library of historical medical images for use by the applications discussed herein.

Figure 12:
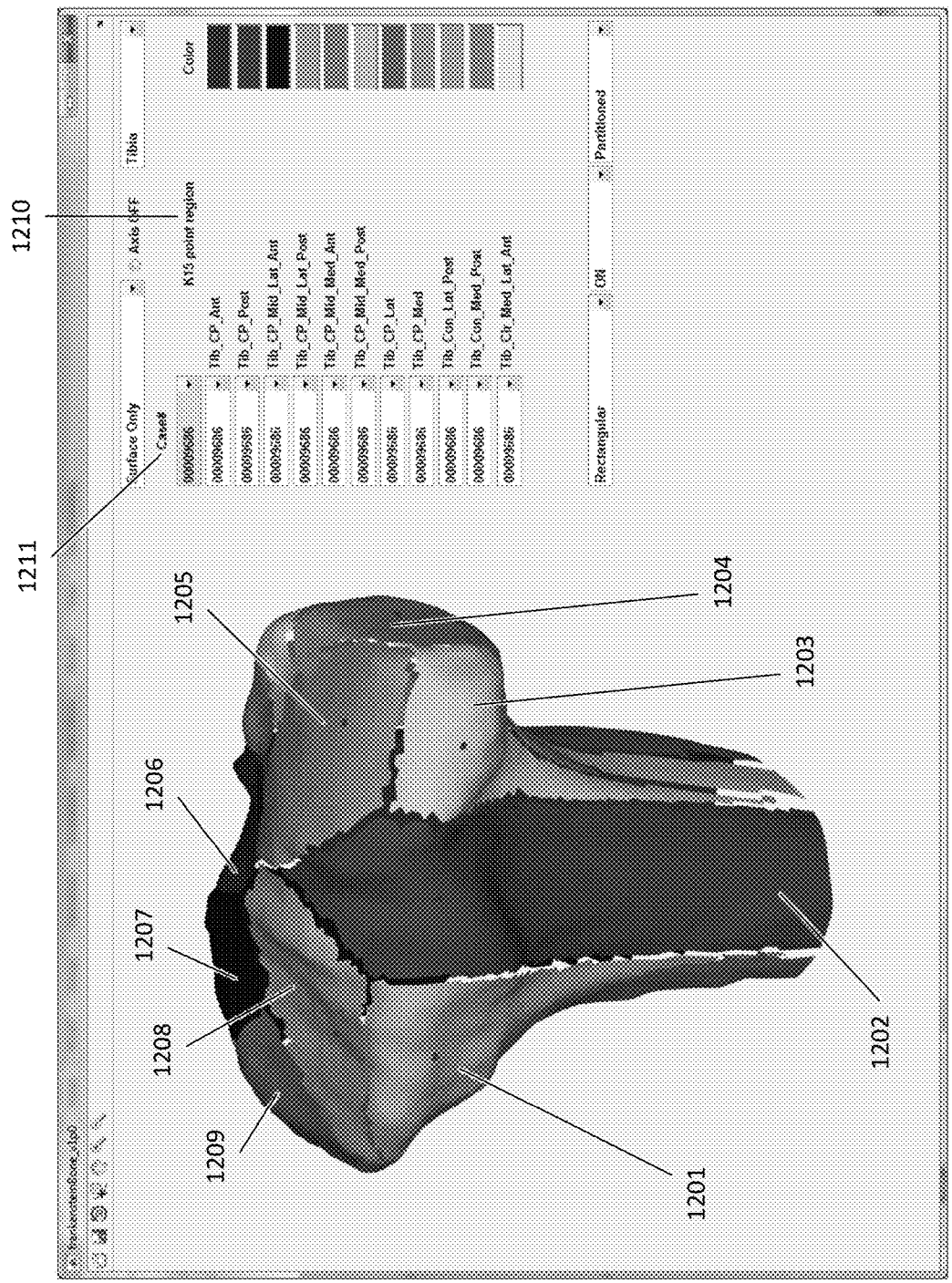
FIG. 12 depicts an illustrative example of a generated 3D model in accordance with an embodiment.

In an embodiment, once a historical image has been found that closely matches each segmented (e.g., fragmented, partitioned, etc.) portion 105, the various 3D image data can be compiled and/or combined to create a hypothetical 3D model of patient's anatomy 106, such as the model shown in FIG. 12. When the fragments are combined the areas where two or more fragments meet may be normalized or smoothed. As each fragment is processed, a statistical analysis may be performed to generate the most accurate and normalized patient anatomy (e.g., the surface of a patient's bone), ensuring the simulated bone is consisted with the shape(s) of typical bones. In a further embodiment, once the anatomical feature (e.g., bone surface) has been properly combined, a 3D model may be generated 106.

It should be understood that various alternative embodiments are also possible. For example, bone segmentation may not be performed in an embodiment. In this embodiment, a case processing engineer and/or end-user (e.g., a surgeon or other hospital staff) may match the patient's anatomical feature (e.g., bone) to the x-rays using the 3D images of other scans. In a further embodiment, the 3D images of the other scans may be combined with one or more x-ray images. In another embodiment, a synthetic 2D image (e.g., an image generated from a library of known 3D patient bone models) may be generated that matches the patient's 2D images (e.g., A-P x-rays, M-L x-rays, etc.).

In additional embodiments, the historical image library may include segmented bone models, and a user may rely on such models to serve as a surrogate for any subsequent segmentation that would may be needed. Moreover, some embodiments may rely on an outline and/or silhouette. In various other embodiments, the patient's anatomical features may not necessarily be recreated in its entirety. Thus, in some embodiments, a glove-type fit may be created. In other embodiments only discrete arms, pads, and/or other contact features may be included. In further embodiments, some or all of the pre-operative decisions depicted in the pre-op plan, such as, for example, the size, position, and potential pin-hole locations or cut slots may also be represented. In some embodiments, a functional approximation may be created, such that a surgeon or medical staff member has sufficient information to identify location information for a cutting slot, bone marker, pin, cut guide, or the like. As discussed herein, various guides may exist or be used with the embodiments discussed herein. As would be understood by someone of ordinary skill in the art, a guide or alignment tool maybe referred to, herein and in the art, as a variable bone coupler.

As discussed herein, surgically pertinent aspects of a patient feature (e.g., a bone, ligament, cartilage, etc.) may be estimated, rather than forming a comprehensive recreation of the entire feature. Thus, it may not be required to create a complete or full model in some embodiments. Those having ordinary skill in the art will understand that creating 3D geometry from MRI or CT is a known process. However, creating a 3D model from 2D images is less straightforward. Thus, the embodiments disclosed herein, should not be compared to 3D reconstructions using such 3D image capturing systems. Rather, the various embodiments discussed herein more closely relates to a system that uses two or more 2D views.

It is foreseeable that at least some variable bone coupler guides may still be rapid-manufactured and single-use. Thus, in some embodiments, options may be provided for the end-user to adjust a size of a suggested variable bone coupler configuration or otherwise revise the instrument. For example, the user can remove a physical (e.g., manufactured) contact point, such as, by breaking off a tab or folding a surface over if the contact point does not seem appropriate. Similarly, the contacts of a variable bone coupler could be raised to increase the resection depth if the user deems the resection depth to be too shallow. In a further embodiment, the contact point or tab (i.e., feature) may be removed or adjusted to allow for existing soft tissue (e.g., meniscus and/or other remnant soft tissue).

Thus, in some embodiments, a repositioning of a custom guide may be possible not only before manufacturing, but also at the time of surgery. In other words, fine adjustment of the cut guide may be optional. As discussed herein extremely high accuracy and precision, which is one of the major drawbacks of the current patient specific instrumentation market, may not be required. Thus, an improved system and method for approximation of a patient's anatomy that is sufficient for various functions, is described herein. If an end user, such as a surgeon, finds the instrument to be sub-optimal, the end user may make minor adjustments (e.g., removing a contact point) to allow additional degrees of freedom.

Accordingly, the embodiments discussed herein generally relate to an automated, or semi-automated, software tool that can create a 3D representation of a patient's anatomy (e.g., bone and articular cartilage) based on a plurality of bi-planar images. In some embodiments, the model is partitioned into subdivided surfaces (i.e., sub-surfaces) and selectively manipulated by a system, or a user, to adjust the working model to match the received 2D images 101. In some embodiments, the target shape of the model may be dictated by 2D images of the patient's anatomy. In a further embodiment, fine-tuning of the patient's anatomy (e.g., one or more bones) may leverage information gleaned from the starting point bone. That is, in each corresponding area of the bone model, characteristics (e.g., parameters derived) from that area of the initial bone can be used to determine how one or more adjustments are applied. In some embodiments, the 2D images may be used as a measurement tool, even if/when the points and/or segments are outside the radiographs. In another embodiment, the points may best represented on the bone (e.g., non-cartilaginous area), and/or areas most perpendicular to the radio graph may be repositioned in the 2D image, thereby helping determine the remaining bone geometry.

An illustrative example will now be discussed in which the anatomical model is a joint, such as a knee, shoulder, or hip. However, it should be understood that the model could represent various other aspects of the bony anatomy or soft tissue. Potential imaging modalities utilized for creation of an anatomical model may include MRI, CT, x-ray, DEXA, PET, ultrasound, etc. As discussed, the anatomical model may be subsequently subdivided or partitioned into a number of discrete volumes, as shown in the images below. Division of the model surfaces creates a library of similarly sub-divided bone shapes. Each of the segments in the model will have a characteristic shape with transition to neighboring segments.

Figure 3:
FIG. 3 depicts another illustrative example of one or more 2D medical images in accordance with an embodiment.

It should be understood that although FIGS. 2-11 depict a user interface in which the images are displayed for viewing and/or editing, no user interface or display is required. Rather, some embodiments may be fully automated and require no human intervention or adjustment. FIGS. 2A and 2B illustrate example 2D medical images received by a disclosed system. As shown, FIG. 2A is an anterior-posterior image of the right knee of a patient while standing (i.e., load bearing). FIG. 2B shows a lateral image of the same knee. It should be understood that additional images (e.g., a standing lateral oblique) may also be present and that FIGS. 2A and 2B are merely exemplary. FIG. 3 shows an example display 300, which comprises various additional 2D patient images 301, 302, 303, 304, 305, and 306, wherein image 303 is selected for display in window 310.

Figure 4:
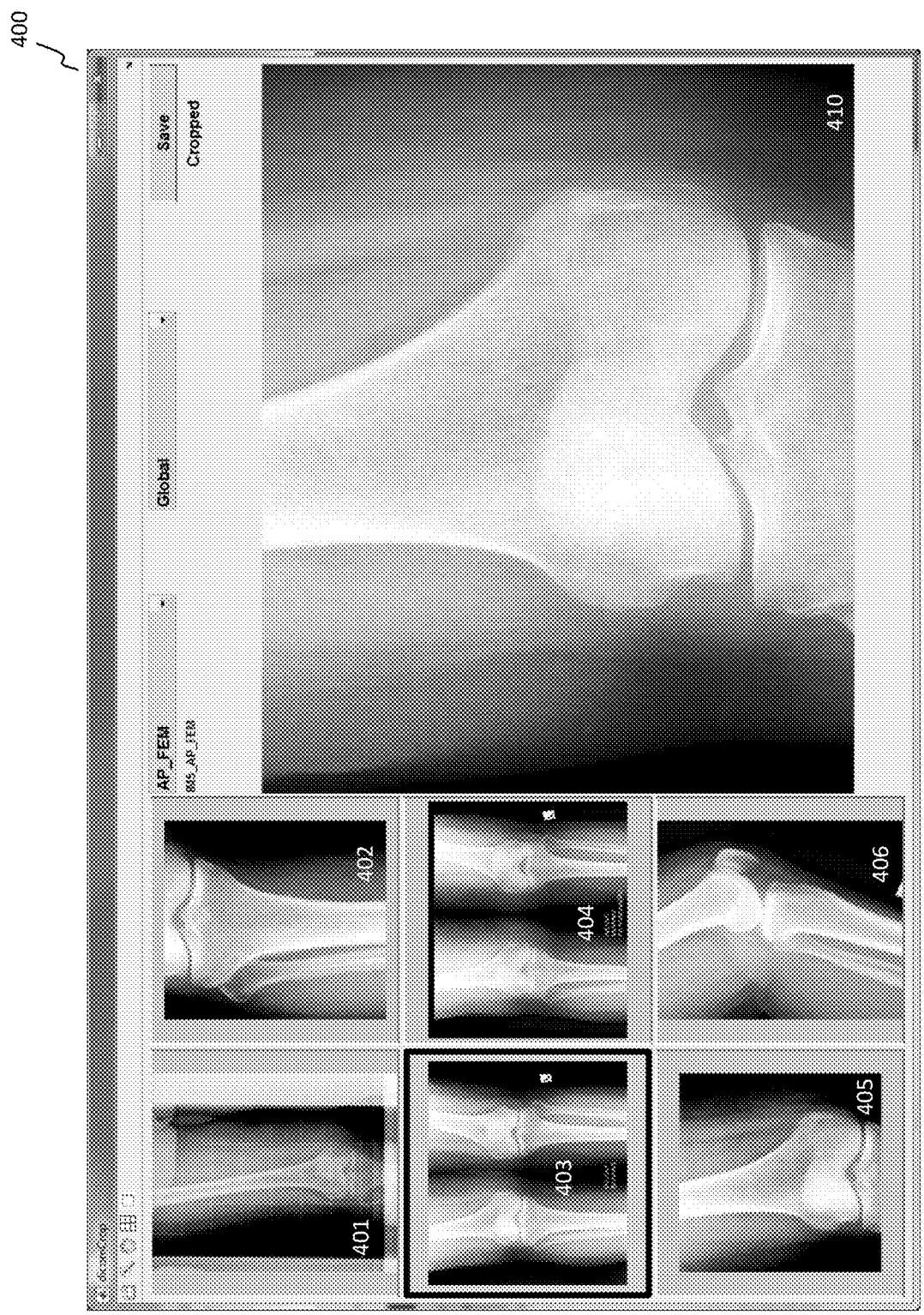
FIG. 4 depicts another illustrative example of one or more 2D medical images in accordance with an embodiment.
Figure 5:
FIG. 5 depicts another illustrative example of one or more 2D medical images in accordance with an embodiment.
Figure 6:
FIG. 6 depicts another illustrative example of one or more 2D medical images in accordance with an embodiment.

Referring now to FIG. 4, a user interface 400 is shown in which the selected FIG. 403 has been altered. More particularly, the image 410 has been enlarged to focus on the knee joint and has been cropped to enhance image analysis and placement of the plurality of points (e.g., K15 points, adaptively or CAD derived points, etc.). In FIG. 5, a new image 506 of the joint has been selected in the user interface 500 for display in display window 510. Similar to FIG. 4, FIG. 6 shows a user interface 600 with an altered or modified view 610 of the selected image 606. Thus, as discussed herein, various processing (e.g., zooming, cropping, rotating, etc.) may be needed in order to best enhance image analysis by a user.

Figures 7A, 7B:
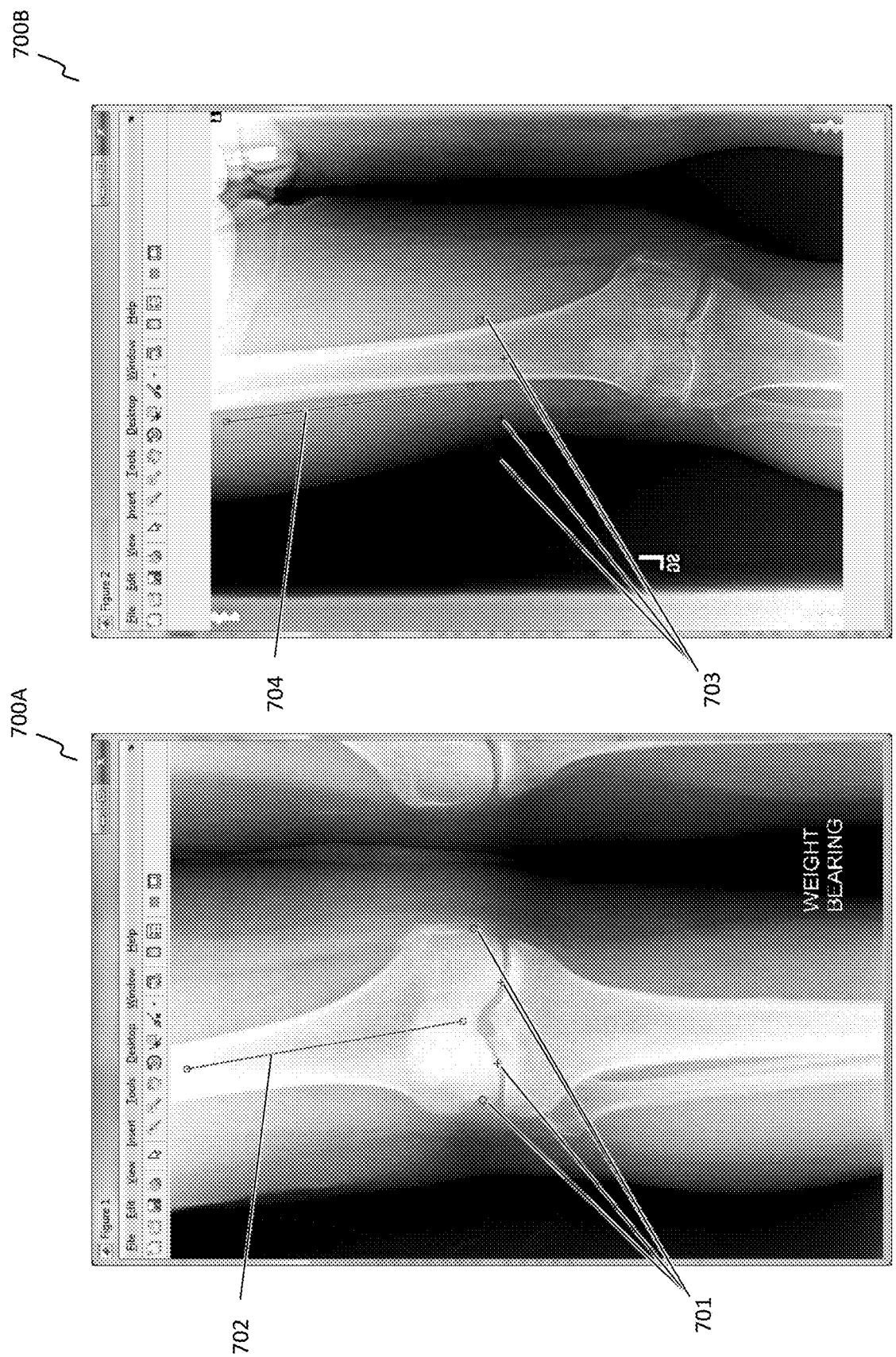
FIG. 7A depicts another illustrative example of one or more 2D medical images in accordance with an embodiment.
FIG. 7B depicts another illustrative example of one or more 2D medical images in accordance with an embodiment.

In FIGS. 7A and 7B, an example of the image analysis is shown. In some embodiments, a historical medical image (i.e., example femur) 700A may be identified as being roughly similar to a received 2D image (i.e., femur under test) 700B. Accordingly, as discussed herein, a plurality of points (e.g., four) K15 points 701 may be identified in the historical medical image 700A. Additionally, in some embodiments, an anatomical line 702 may also be present. Although the image 700B in FIG. 7B was processed, the image may still not properly aligned with the K15 points 703 and the anatomical line 704, which are designed to replicate the points and line of FIG. 7A (i.e., the historical image).

In an embodiment, an accurate corresponding point 703 may be located or identified for each point 701. FIG. 8 depicts the user interface after such correction has been performed. As such, the plurality of points 801 and 803 and the anatomical alignment lines 802 and 804 can now be directly compared to verify the accuracy and best fit of the selected historical image 800A to the test image 800B.

Figure 9:
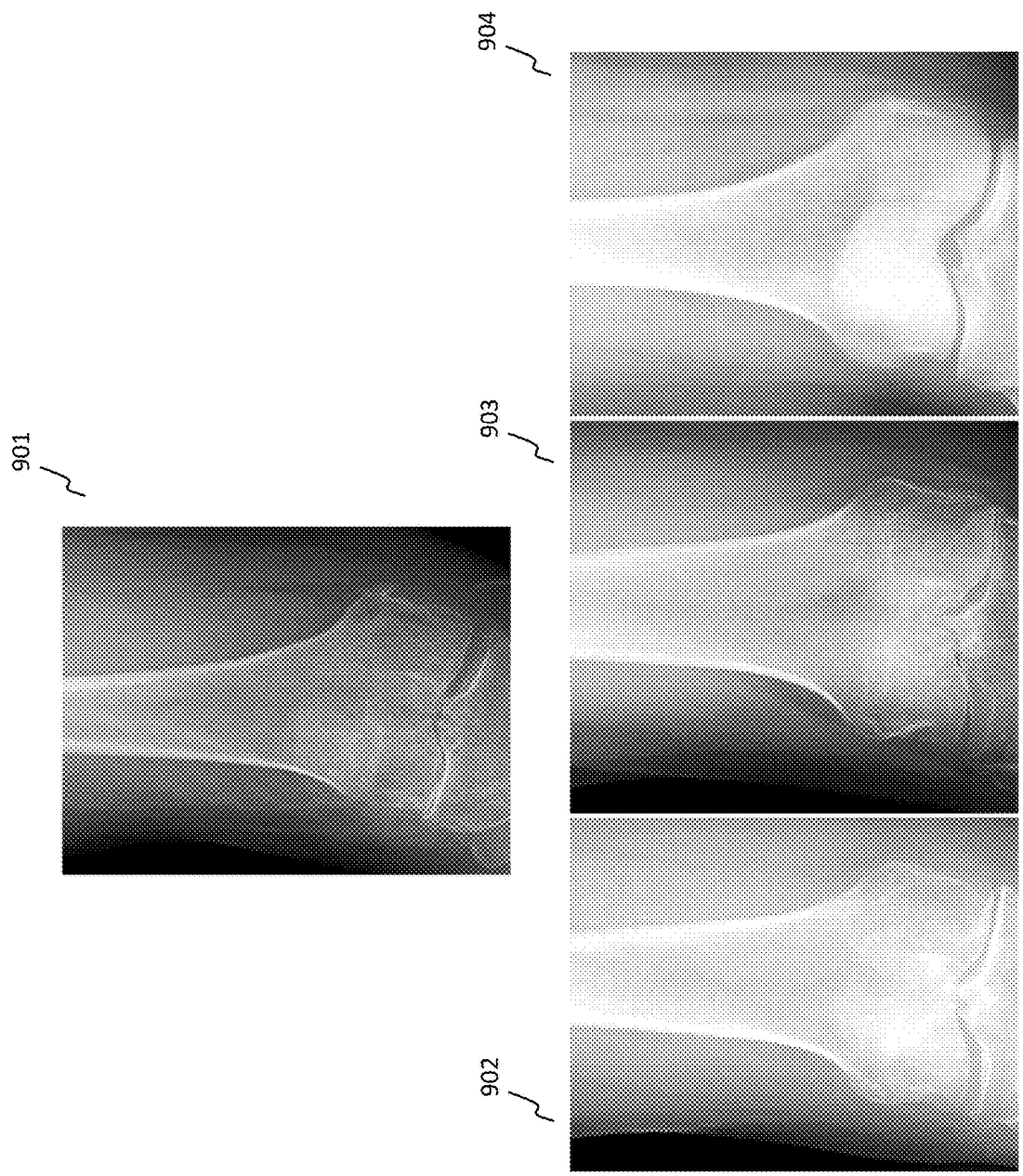
FIG. 9 depicts another illustrative example of one or more 2D medical images in accordance with an embodiment.
Figure 10:
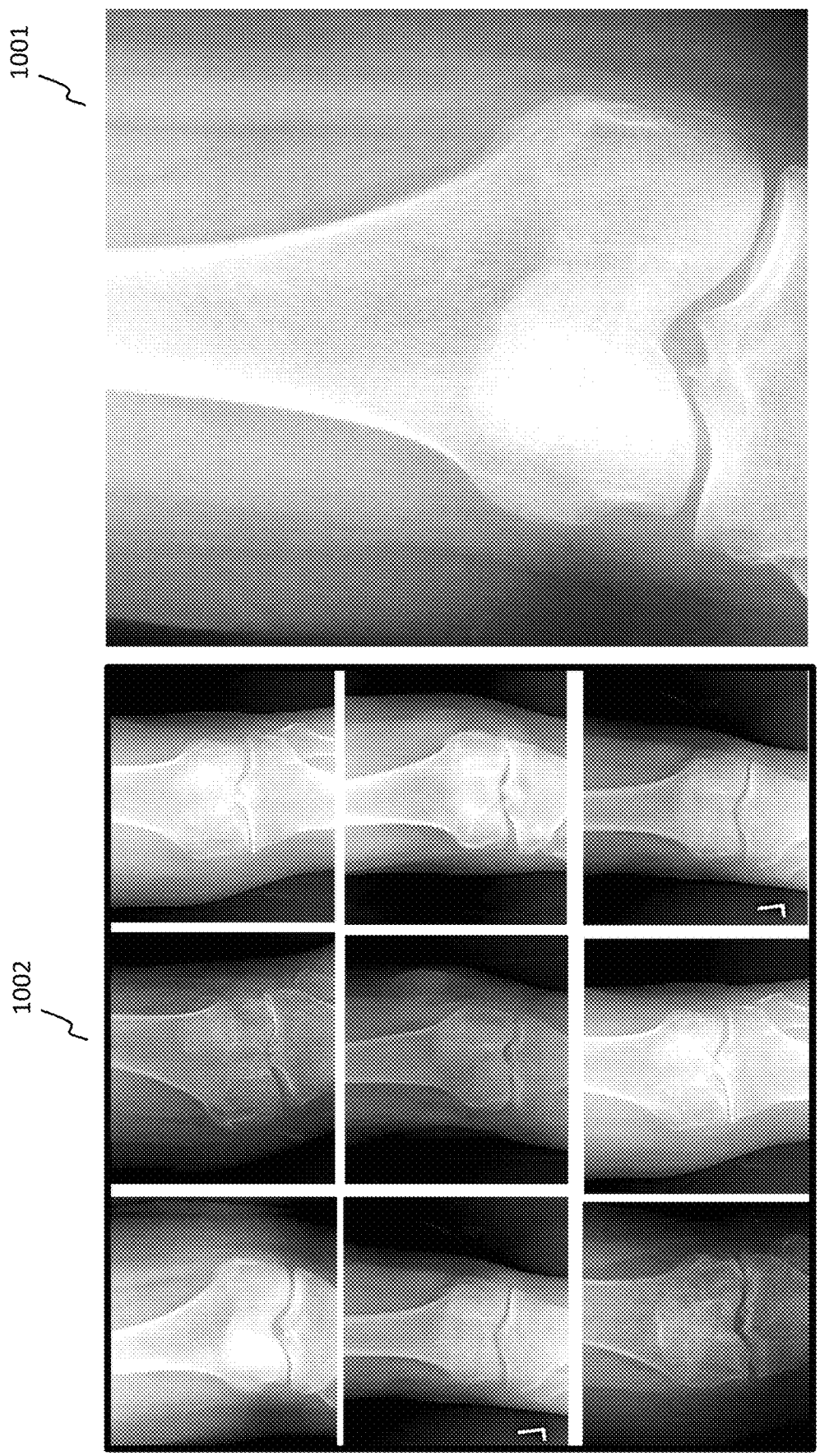
FIG. 10 depicts another illustrative example of one or more 2D medical images in accordance with an embodiment.

Although the points 801/803 and the lines 802/804 may appear to be similar, additional 2D images may also be considered as viable candidates. As shown in FIG. 9, a plurality of potential matches 902, 903, and 904 to the test case 901 may be identified. In a further embodiment, all of the historical images, as well as the test image may be further modified to select a correct orientation (e.g., using a toggle method, progressive refinement method, or augmented with stereolithograpy). In some embodiments, additional potential matches may be further identified based on known similarities within the historical library. In other words, once a plurality of potential candidate sets are determined, an embodiment may use a statistical analysis method to identify additional candidates based solely on already identified historical images 902-904. As shown in FIG. 10, additional potential candidates 1002 may be identified.

Figure 11:
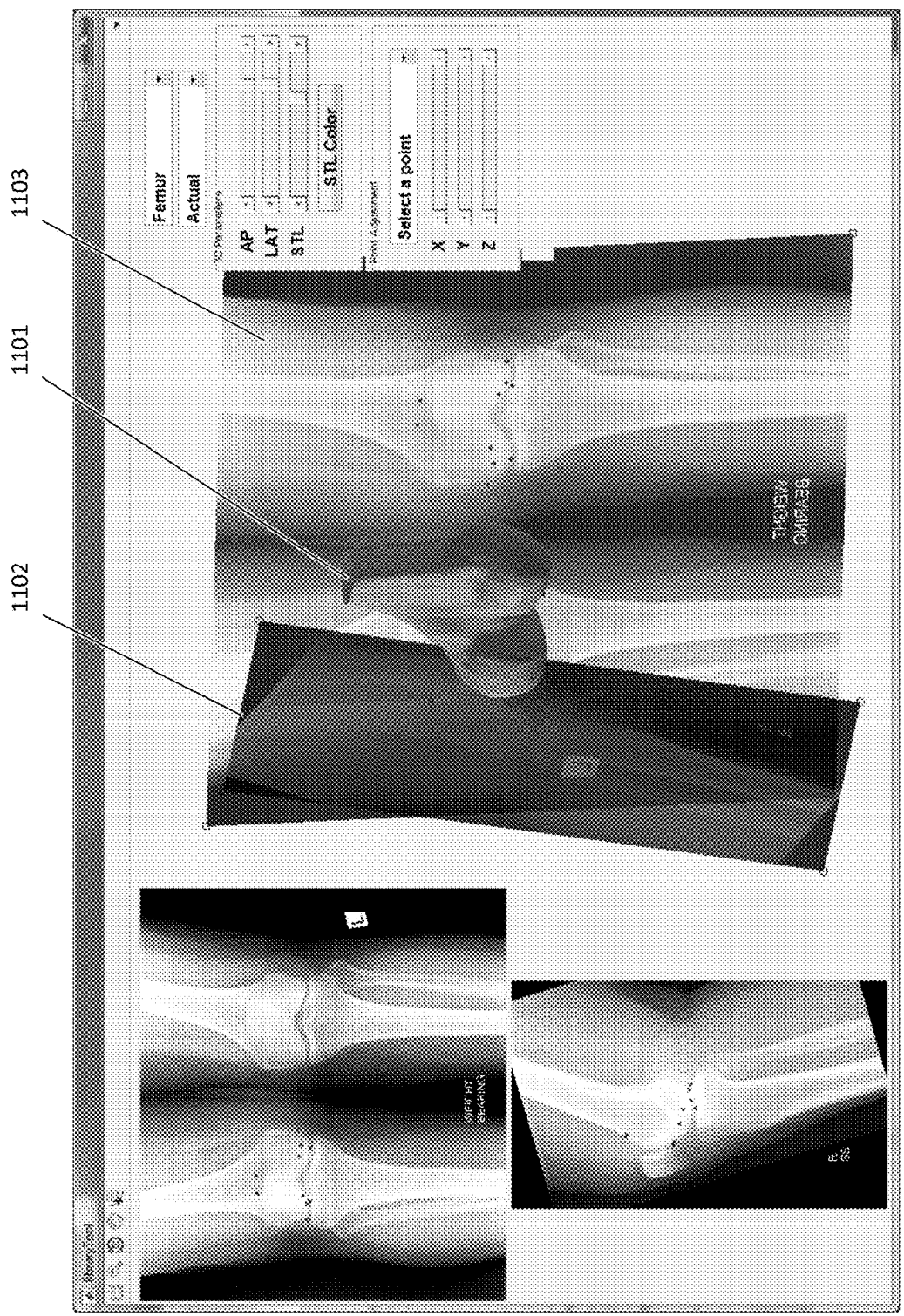
FIG. 11 depicts an illustrative example of one or more 2D medical images overlaid with a generated 3D model in accordance with an embodiment.

Referring now to FIG. 11, an example user interface is shown in which each area associated with a point (e.g., K15 points) has been matched to a level that exceeds a determined threshold. Thus, an initial or rough 3D model 1101 may be created. In some embodiments, the points may be projected onto the 3D bone where they intersect with the surface.

Moreover, in some embodiments, the original 2D images 1102 and 1103 may be overlaid, or super-imposed, on the newly created 3D model to enable a user to move the 3D model relative to the 2D images and ensure that no major errors are present. In some embodiments, the 3D model may remain stationary and the 2D images may be moved in relation to the 3D model. In a further embodiment, the movement of the 2D or 3D images may be automated and potential problem areas may be identified autonomously or automatically. In another embodiment, the 2D images may have a known position relative to each other, such that, for example, 2D images 1102 and 1103 may be placed in the proper orientation and angle relative to each other.

Figure 13:
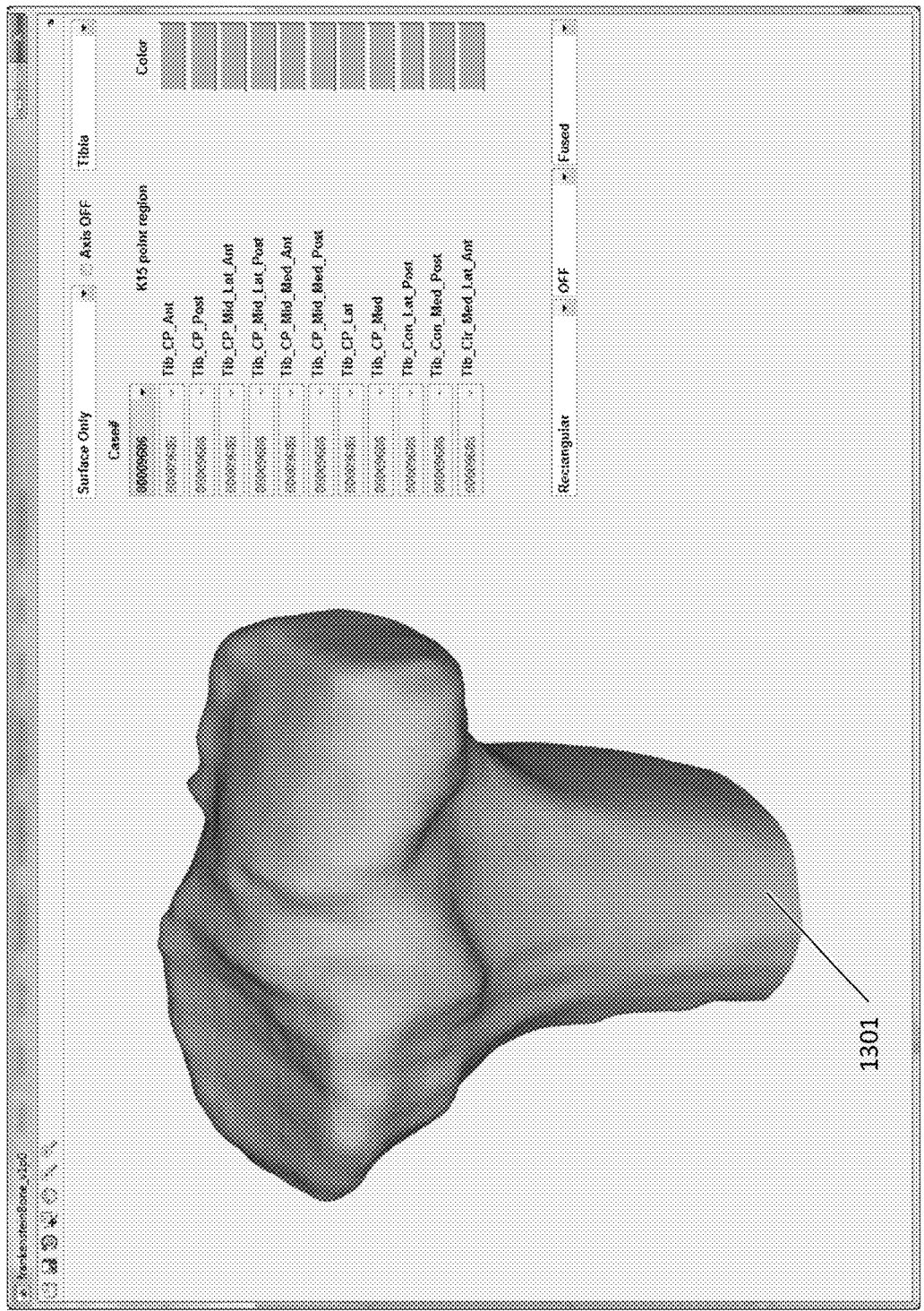
FIG. 13 depicts another illustrative example of a generated 3D model in accordance with an embodiment.

As shown in FIG. 12. once the best-matching historical images are selected for each sub-section of bone, each portion 1201, 1202, 1203 . . . 1209 may be combined together. As shown, each point region 1210 may be identified by anatomic landmark (e.g., CP_Ant, CP_Post, CP_Mid_Lat_Ant, etc.) and historical case number 1211. Once all of the sub-sections are combined, additional fine tuning adjustments may be made to ensure that no deformities or irregularities exist at each intersection of the two sub-sections. Thus, through a normalization process the 3D model may be converted from multiple sub-sections into a single 3D model 1301, such as that shown in FIG. 13.

In another embodiment, the transition region (e.g., seams) between sub-sections, and therefore the net shape of the bone model, may be governed by a spatial mapping between the points (e.g., K15 points), surface tangencies of the segments, pixel/voxel grayscale values of image data, edge detection values between pixels/voxels, models/curves that are representative of the segment surfaces, or some combination thereof. In a further embodiment, the spatial mapping may be provided as inputs to one or more of deep learning or machine learning techniques, including the use of convolutional neural networks. In such an embodiment, a neural network may be trained utilizing various image data including MRI scans and MRI-derived 3D models that have been parameterized with control points (e.g., K15 points) and a corresponding correlation matrix, as well as 2D x-ray data.

Figure 17:
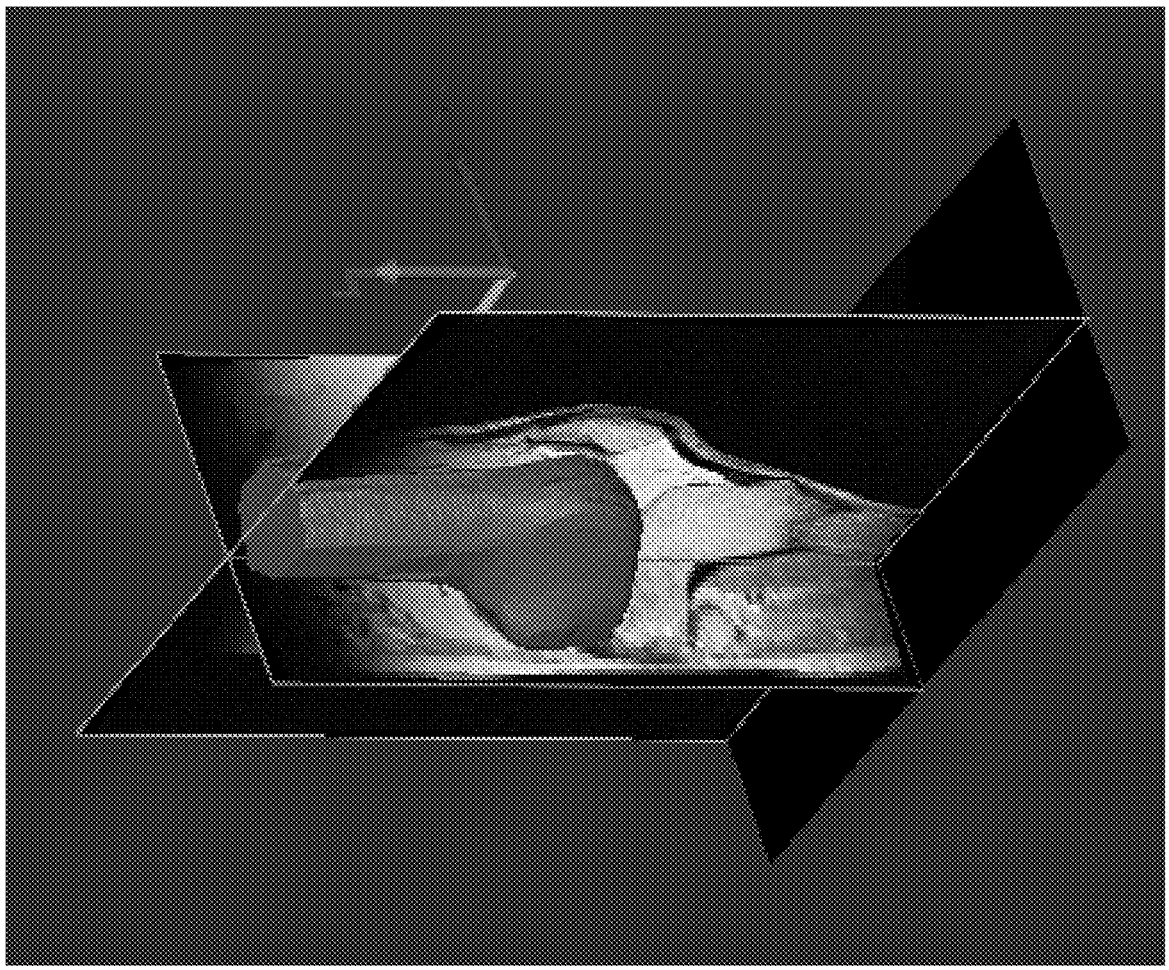
FIG. 17 depicts another illustrative example of a generated 3D model overlaid on the registered 2D images in accordance with an embodiment.

As an additional example, a patient scheduled for total knee replacement has received x-ray imaging of the affected knee. As discussed herein, complemenatary views of x-ray images, (e.g., anterior-posterior images, lateral images, two images that are roughly about 80° to 100° (i.e., normal or perpendicular) to each other of the joint may be captured and sent to an imaging center via a predetermined data transfer protocol. At the imaging center, the x-ray images may be registered to one another by either manual or automated techniques described herein. An anatomical model of the bone that exhibits a coarse correspondence to the x-ray images (e.g., a coarse model) may be overlaid on the registered 2D images as shown in FIG. 17. In this example, the coarse model is an anatomical model of bone or a portion of bone that is selected from a library of previously segmented bone models.

In some example embodiments, the coarse model may be specified based on a series of landmarks that correspond to features identified in the 2D x-ray images, and a imaging technician may manipulate one or more control points (e.g., K15 points) to improve upon the correspondence of the model to the 2D images. Software may be used to produce a model containing various bone segments from the input library and to create segment transitions based on predetermined correlations and interpolation operations. In a further embodiment, the 3D model may subsequently be used to model and manufacture a variable bone coupler for the patient's knee replacement surgery.

As discussed herein, a coarse bone model may be based on a selection from a collection of actual bone geometries and not a statistical model. Thus, in some embodiments, landmarks on the bones may be used as a means of selecting the bone that most resembles the bone depicted by the x-rays. Those having ordinary skill in the art would understand that landmarks may be, for example, epicondyles, the tibial spine, Whiteside's line, the trans-epicondylar axis, tibial tuberosity, a mechanical axis, an anatomic axis, the medial malleolus, or an adductor tubercle. Alternatively, a statistical model may be used. However, a statistical model may have the drawback of overly smoothing the bone.

As discussed, the coarse model may only be a first-order solution or a starting point. Thus, additional fine-tuning may be performed. In some embodiments, a statistical approach that does not include a mean-bone statistic may be used. Generally, a closed-form optimization that leverages input data (e.g. points on an initial x-ray) and matches it to the library of solutions may make use of statistics from the historical library, at least to aid in finding a maximally likely selection. Thus, statistics (e.g., statistical analysis of the signature or thumbprint of the bone) are used in certain embodiments.

Figure 14:
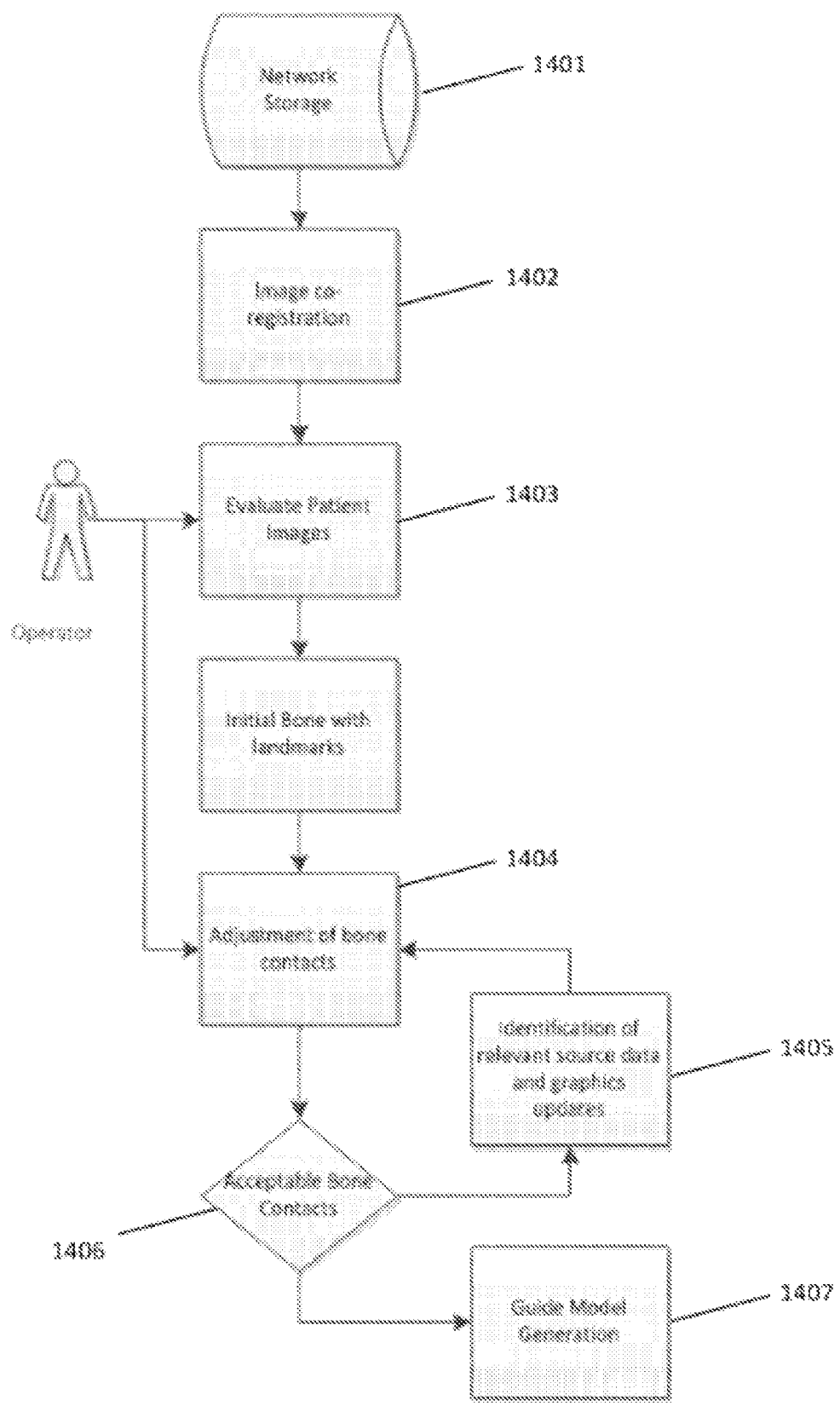
FIG. 14 depicts an illustrative method for guide model generation via 2D to 3D intuition.

FIG. 14 depicts a flowchart for a process of generating the variable bone coupler via 2D to 3D intuition. In step 1401, 2D images and a coarse model are retrieved from network storage. In step 1402, the 2D images and the coarse model are registered in a coordinate system. In step 1403, a user evaluates the coarse model in comparison to the 2D images, and manipulates the coarse model to align specific landmarks of the 2D images. In step 1404, the user manipulates bone contact locations (e.g., adaptive points, visual handles, etc.) of the coarse model. In step 1405, the user iteratively identifies relevant source data and updates the graphical representation. In step 1406, the user determines whether the bone contact locations are acceptable. In step 1407, the user outputs the guide model.

The distinguishing technical effect of the disclosed embodiments is to provide the ability to quickly create a 3D representation of a patient's joint based on 2D x-ray data without time-consuming or user-intensive operations. Accordingly, the proposed embodiments may begin with a coarse model that is the result of training, using a rich data-set of MRI and x-ray scans. In addition, the process may not be fully automated (i.e., it may still require fine tuning adjustments and approval from an imaging expert). These features allow for a bifurcated delivery model that supports design and manufacture of the guides in both clinical and off-site settings, as presented in FIG. 15.

Figure 15:
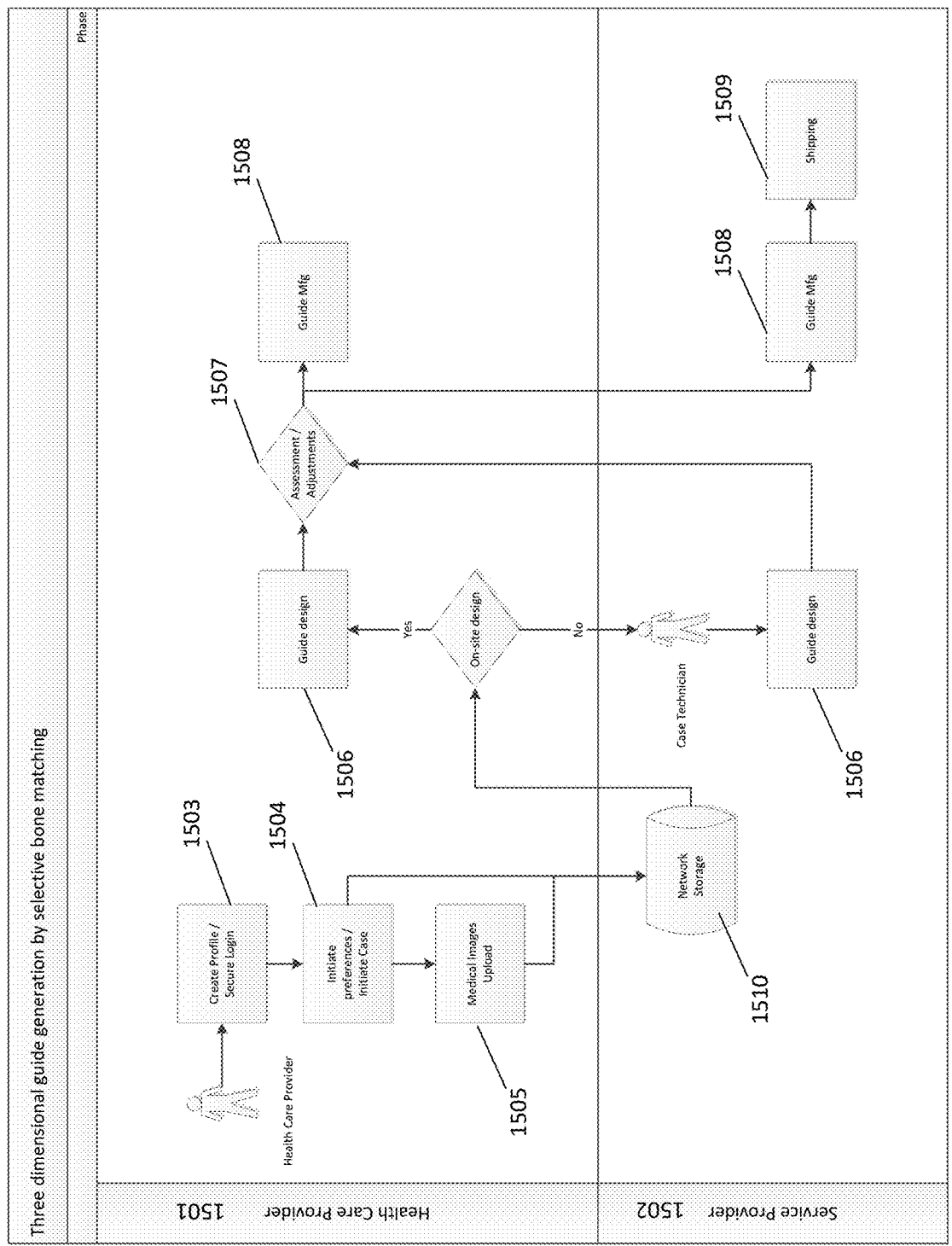
FIG. 15 depicts an illustrative method for surgical guide design and manufacture showing both service-based and HCP-driven models.

FIG. 15 depicts the generation of the variable bone coupler by selective bone matching surgical guide design and manufacture strategy showing both service-based 1502 and health care provider (HCP) driven models 1501. In FIG. 15, certain operations may be performed by a health care provider 1501, such as a surgeon, nurse, hospital, or surgical center, while other operations may be performed by a service provider 1502, such as a manufacturer or engineering design firm. Those of ordinary skill in the art would understand that there may be a plurality of HCPs and/or service providers. In the depicted embodiment, an HCP logs into a system 1503 and creates a patient profile 1504 to initiate a case. In some embodiments, the HCP also may designate initial preferences for a particular patient 1504. As examples, initial preferences may include a surgical approach, desired standard instruments, a desired implant type, or the like. The HCP may upload the patient's x-rays 1505 to a network storage device 1510. The HCP also may upload the patient profile (not shown). Although the network storage device 1510 is shown as being located within the service provider's 1502 domain, it should be understood that the HCP1507 may alternatively control the network storage device 1510.

In some embodiments, a case technician may retrieve information from the network storage device 1510 and design 1506 and build the variable bone coupler. The variable bone coupler is iteratively assessed and adjusted as needed. The variable bone coupler may then be manufactured 1508. In some embodiments, the variable bone coupler may be 3D printed. In some embodiments, the variable bone coupler may be manufactured 1508 by the HCP 1501. Alternatively, the variable bone coupler may be manufactured 1508 by the service provider 1502. If the guide is manufactured by the service provider 1502, then the variable bone coupler may be shipped 1509 to the HCP 1501.

The variable bone coupler resulting from this process may be designed to interface with existing instruments and locate them with a series of discrete contact features (i.e., instead of a congruent, glove-like fit). As a result, the variable bone coupler may be designed by estimating surgically pertinent aspects of the bone, instead of aiming for a comprehensive recreation of the entire bone. In a further embodiment, a patient-matched stylus may be created, in which multiple positioned points (e.g., spring loaded and/or adjustable) are present.

It should be noted that any one of the previously described automated techniques could produce several "close" solutions from which a one or more users select the best representation based on their experience or training in radiological imaging. In a further alternative embodiment, a user may manipulate characteristic curves associated with each bone segment shape instead of control points. Such an embodiment could be facilitated using both automated and semi-automated techniques.

The previously disclosed embodiments are presented in the context of total knee arthroplasty instrumentation. It should be appreciated that similar techniques can be used to create instrumentation for the reconstruction of other joints including, but not limited to, the hip, ankle, and shoulder. Furthermore, the image registration techniques could be applied to patient specific implant design. For example, the resulting 3D anatomical models could be used for design of a custom flange acetabular component for total hip arthroplasty, or custom cranial, facial, or mandibular components.

Various embodiments described herein may be applicable to other areas of orthopaedic medicine including trauma extremity reconstruction, and spine. In the trauma space, 2D to 3D conversion could be used to create models of long bones. These models could facilitate the manufacture of patient specific osteotomy guides for segmental defect removal, limb lengthening, limb deformity correction, high-tibial osteotomy, etc. Furthermore, the 3D models could be used as fracture guides to restore alignment in the long bones and/or wrist after injury. In some embodiments, the 3D models may be used for patient specific pedicle screw guides and custom 3D printed spinal cages.

There are also opportunities to utilize alternate embodiments in the sports medicine space. Specifically, 2D to 3D conversion could be used to create patient specific guides for ligament tunneling used in ACL reconstruction and similar procedure, and/or bone preparation for focal-defect repair.

Computer readable program instructions for carrying out operations disclosed herein may include assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider).

Aspects of the present invention are described herein with reference to flowchart illustrations and/or block diagrams of methods, apparatuses (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which are executed on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 16:
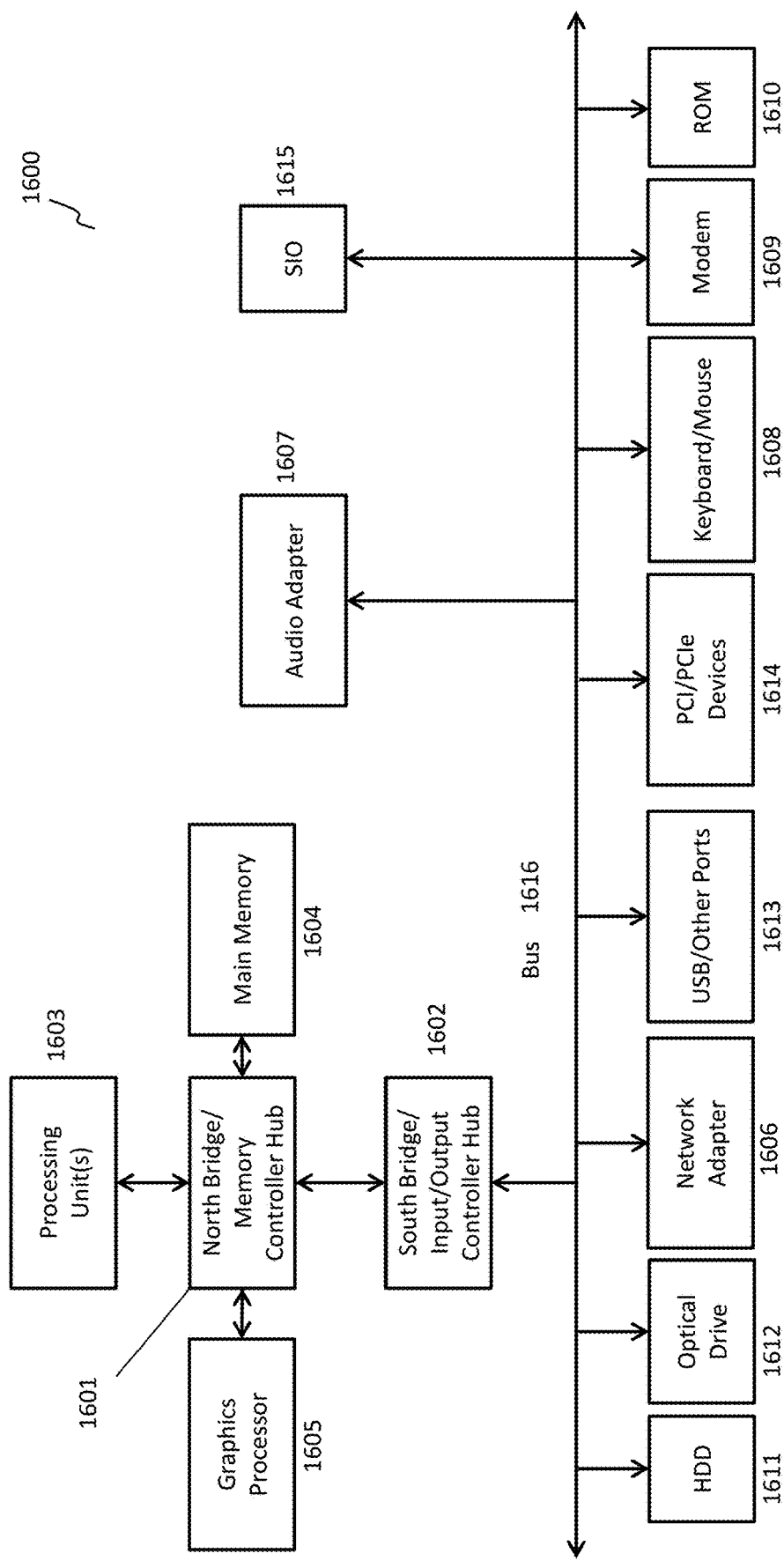
FIG. 16 depicts an illustrative computer system for creating 3D anatomical models from bi-planar 2D images.

FIG. 16 is a block diagram of an example data processing system 1600 in which aspects of the illustrative embodiments are implemented. Data processing system 1600 is an example of a computer, such as a server or client, in which computer usable code or instructions implementing the process for illustrative embodiments of the present invention are located. In one embodiment, FIG. 16 may represent a server computing device.

In the depicted example, data processing system 1600 can employ a hub architecture including a north bridge and memory controller hub (NB/MCH) 1601 and south bridge and input/output (I/O) controller hub (SB/ICH) 1602. Processing unit 1603, main memory 1604, and graphics processor 1605 can be connected to the NB/MCH 1601. Graphics processor 1605 can be connected to the NB/MCH 1601 through, for example, an accelerated graphics port (AGP).

In the depicted example, a network adapter 1606 connects to the SB/ICH 1602. An audio adapter 1607, keyboard and mouse adapter 1608, modem 1609, read only memory (ROM) 1610, hard disk drive (HDD) 1611, optical drive (e.g., CD or DVD) 1612, universal serial bus (USB) ports and other communication ports 1613, and PCI/PCIe devices 1614 may connect to the SB/ICH 1602 through bus system 1616. PCI/PCIe devices 1614 may include Ethernet adapters, add-in cards, and PC cards for notebook computers. ROM 1610 may be, for example, a flash basic input/output system (BIOS). The HDD 1611 and optical drive 1612 can use an integrated drive electronics (IDE) or serial advanced technology attachment (SATA) interface. A super I/O (SIO) device 1615 can be connected to the SB/ICH 1602.

An operating system can run on processing unit 1603. The operating system can coordinate and provide control of various components within the data processing system 1600. As a client, the operating system can be a commercially available operating system. An object-oriented programming system, such as the Java™ programming system, may run in conjunction with the operating system and provide calls to the operating system from the object-oriented programs or applications executing on the data processing system 1600. As a server, the data processing system 1600 can be an IBM® eServer™ System p® running the Advanced Interactive Executive operating system or the Linux operating system. The data processing system 1600 can be a symmetric multiprocessor (SMP) system that can include a plurality of processors in the processing unit 1603. Alternatively, a single processor system may be employed.

Instructions for the operating system, the object-oriented programming system, and applications or programs are located on storage devices, such as the HDD 1611, and are loaded into the main memory 1604 for execution by the processing unit 1603. The processes for embodiments described herein can be performed by the processing unit 1603 using computer usable program code, which can be located in a memory such as, for example, main memory 1604, ROM 1610, or in one or more peripheral devices.

A bus system 1616 can be comprised of one or more busses. The bus system 1616 can be implemented using any type of communication fabric or architecture that can provide for a transfer of data between different components or devices attached to the fabric or architecture. A communication unit such as the modem 1609 or the network adapter 1606 can include one or more devices that can be used to transmit and receive data.

Those of ordinary skill in the art will appreciate that the hardware depicted in FIG. 16 may vary depending on the implementation. Other internal hardware or peripheral devices, such as flash memory, equivalent non-volatile memory, or optical disk drives may be used in addition to or in place of the hardware depicted. Moreover, the data processing system 1600 can take the form of any of a number of different data processing systems, including but not limited to, client computing devices, server computing devices, tablet computers, laptop computers, telephone or other communication devices, personal digital assistants, and the like. Essentially, data processing system 1600 can be any known or later developed data processing system without architectural limitation.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112(f) unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as they fall within the true spirit and scope of the invention.

The invention claimed is:

1. A method comprising:
   receiving, by a processor, one or more 2D images of an anatomical feature of a patient;
   identifying a plurality of points within the one or more 2D images, wherein each point is associated with a landmark of the anatomical feature;
   segmenting, by the processor, the one or more 2D images into a plurality of image fragments based on the plurality of identified points;
   for each of the plurality of image fragments, searching a library of historical 2D images having associated 3D images, for a closest match to the 2D image fragment of the anatomical feature of the patient; and
   joining, by the processor, the 3D images associated with each of the closest matches to form a model of the anatomical feature of the patient;
   wherein the areas where in the 3D images are joined are normalized or smoothed.

2. The method of claim 1, wherein the anatomical landmark comprises at least one of an epicondyle, tibial spine, Whiteside's line, trans-epicondylar axis, tibial tuberosity, a mechanical axis, an anatomic axis, a medial malleolus, and an adductor tubercle.

3. The method of claim 1, wherein the one or more 2D images of the anatomical feature comprise at least two 2D images, and wherein the at least two images are oblique to a third 2D image.

4. The method of claim 1, wherein the one or more 2D images of the anatomical feature comprise at least one coronal view image and at least one sagittal view image.

5. The method of claim 4, wherein the at least one coronal view comprises at least one of an anterior-to-posterior view and a posterior-to-anterior view.

6. The method of claim 4, wherein the at least one coronal view comprises at least one of a load bearing view and a non-load bearing view.

7. The method of claim 4, wherein the at least one sagittal view comprises at least one of a lateral-to-medial view and a medial-to-lateral view.

8. An information handling device comprising:
   a processor; and
   a non-transitory, processor-readable storage medium that stores instructions executable by the processor to:
   receive one or more 2D images of an anatomical feature of a patient;
   identify a plurality of points within the one or more 2D images, wherein each point is associated with a landmark of the anatomical feature,
   segment, based on the plurality of points, the anatomical feature within the one or more 2D images into a plurality of image fragments;
   search, for each of the plurality of image fragments, a library of historical 2D images having associated 3D images, for a closest match to the 2D image fragment of the anatomical feature of the patient; and
   join the 3D images associated with each of the closest matches to form a model of the anatomical feature of the patient;
   wherein the areas where in the 3D images are joined are normalized or smoothed.

9. The information handling device of claim 8, wherein the anatomical landmark comprises at least one of an epicondyle, tibial spine, Whiteside's line, trans-epicondylar axis, tibial tuberosity, a mechanical axis, an anatomic axis, a medial malleolus, and an adductor tubercle.

10. The information handling device of claim 8, wherein the one or more 2D images of the anatomical feature comprise at least two 2D images, and wherein the at least two images are oblique to a third 2D image.

11. The information handling device of claim 8, wherein the one or more 2D images of the anatomical feature comprise at least one coronal view image and at least one sagittal view image.

12. The information handling device of claim 11, wherein the at least one coronal view comprises at least one of an anterior-to-posterior view and a posterior-to-anterior view.

13. The information handling device of claim 11, wherein the at least one coronal view comprises at least one of a load bearing view and a non-load bearing view.

14. The information handling device of claim 11, wherein the at least one sagittal view comprises at least one of a lateral-to-medial view and a medial-to-lateral view.

15. A program product comprising:
   a non-transitory storage device having code stored therewith, the code being executable by a processor and comprising:
      code that receives one or more 2D images of an anatomical feature of a patient;
      code that identifies a plurality of points within the one or more 2D images, wherein each point is associated with a landmark of the anatomical feature;
      code that segments, based on the plurality of identified points, the one or more 2D images into a plurality of image fragments,
      code that searches, for each of the plurality of image fragments, a library of historical 2D images having associated 3D images, for a closest match to the 2D image fragment of the anatomical feature of the patient; and
      code that joins the 3D images associated with each of the closest matches to form a model of the anatomical feature of the patient;
      wherein the areas where in the 3D images are joined are normalized or smoothed.

16. The program product of claim 15, wherein the anatomical landmark comprises at least one of an epicondyle, tibial spine, Whiteside's line, trans-epicondylar axis, tibial tuberosity, a mechanical axis, an anatomic axis, a medial malleolus, and an adductor tubercle.

17. The program product of claim 15, wherein the one or more 2D images comprise at least one coronal view image and at least one sagittal view image.

18. The program product of claim 17, wherein the at least one coronal view comprises at least one of an anterior-to-posterior view and a posterior-to-anterior view.

19. The program product of claim 17, wherein the at least one coronal view comprises at least one of a load bearing view and a non-load bearing view.

20. The program product of claim 17, wherein the at least one sagittal view comprises at least one of a lateral-to-medial view and a medial-to-lateral view.

* * * * *